(12) United States Patent
Argentieri et al.

(10) Patent No.: US 6,348,486 B1
(45) Date of Patent: Feb. 19, 2002

(54) METHODS FOR MODULATING BLADDER FUNCTION

(75) Inventors: Thomas Michael Argentieri, Yardley; Jeffrey Howard Sheldon, Trappe; Mark R. Bowlby, Richboro, all of PA (US)

(73) Assignee: American Home Products Corporation, Madison, NJ (US)

( * ) Notice: Subject to any disclaimer, the term of this patent is extended or adjusted under 35 U.S.C. 154(b) by 0 days.

(21) Appl. No.: 09/977,828

(22) Filed: Oct. 15, 2001

Related U.S. Application Data

(60) Provisional application No. 60/241,078, filed on Oct. 17, 2000, and provisional application No. 60/281,428, filed on Apr. 4, 2001.

(51) Int. Cl.⁷ .................. A61K 31/405; A61K 31/24
(52) U.S. Cl. .................. 514/411; 514/418; 514/535
(58) Field of Search .................. 514/535, 411, 514/418

(56) References Cited

U.S. PATENT DOCUMENTS

| 5,384,330 A | 1/1995 | Dieter et al. |
| 5,565,483 A | 10/1996 | Hewawasam et al. |
| 5,849,789 A | 12/1998 | Rostock et al. |
| 5,852,053 A | 12/1998 | Rostock et al. |
| 5,914,425 A | 6/1999 | Meisel et al. |
| 6,117,900 A | 9/2000 | Rundfeldt |

OTHER PUBLICATIONS

Martin J. Main et al., Molecular Pharmacology, 2000, 253–262, 58.
Rikke Louise Schroder et al., Neuropharmacology, 2001, 888–898, 40.

Primary Examiner—Raymond Henley, III
(74) Attorney, Agent, or Firm—Steven R. Eck

(57) ABSTRACT

This invention provides methods and pharmaceutical compositions for maintaining bladder control or treating urinary incontinence in a mammal utilizing agonists of KCNQ potassium channels, including KCNQ2, KCNQ3, KCNQ4 and KCNQ5 potassium channels, alone or in combination. Compounds useful in these methods include the 1,2,4-triamino-benzene derivatives described in U.S. Pat. No. 5,384,330 (Dieter et al.) and the substituted 3-phenyl oxindole compounds described in U.S. Pat. No. 5,565,483 (Hewawasam et al.). Among the preferred compounds of this invention is N-[2-amino-4-(4-fluorobenzylamino)-phenyl]carbamic acid ethyl ester, also referred to as retigabine.

32 Claims, No Drawings

METHODS FOR MODULATING BLADDER FUNCTION

This application claims priority from copending provisional applications Ser. No. 60/241,078, filed Oct. 17, 2000, and Ser. No. 60/281,428, filed Apr. 4, 2001, the entire disclosures of which are hereby incorporated by reference.

This invention relates to novel methods for modulating bladder tissues utilizing compounds which modulate the KCNQ family of potassium channels, particularly compounds which open or agonize the channels. The methods of this invention include the treatment, prevention, inhibition and amelioration of urge urinary incontinence also known as bladder instability, neurogenic bladder, voiding dysfunction, hyperactive bladder or detrusor overactivity. The methods of this invention also include the prevention and treatment of mixed stress and urge urinary incontinence, including that associated with secondary conditions such as prostate hypertrophy.

BACKGROUND OF THE INVENTION

U.S. Pat. No. 5,384,330 (Dieter et al.) teaches pharmacologically active 1,2,4-triaminobenzene derivatives of the General Formula:

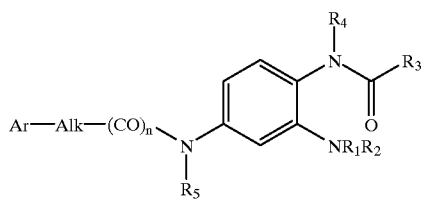

and their properties as anti-epileptic, muscle relaxing, fever-reducing and peripheral analgesic agents.

U.S. Pat. No. 5,565,483 (Hewawasam et al.) teaches compounds of the formulae:

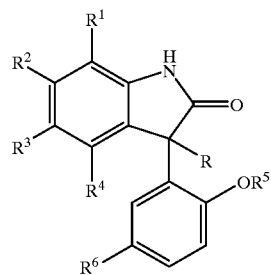

wherein: R is hydrogen, hydroxy or fluoro; $R^1$, $R^2$, $R^3$ and $R^4$ each are independently hydrogen, $C_{1-4}$ alkyl, halogen, trifluoromethyl, phenyl, p-methylphenyl or p-trifluoromethylphenyl; or $R_1$ and $R^2$, $R^2$ and $R^3$ or $R^3$ and $R^4$ are joined together to form a benzo fused ring; $R^5$ is hydrogen or $C_{1-4}$ alkyl; and $R^6$ is chlorine or trifluoromethyl; or a nontoxic pharmaceutically acceptable salt, solvate or hydrate thereof, which are potassium channel openers useful for treating ischemia, convulsions and asthma.

The article Modulation of KCNQ2/3 Potassium Channels by the Novel Anticonvulsant Retigabine, Main et al., Molecular Pharmacology, 58: pp. 253–262, 2000, describes the actions of retigabine (D23129; N-[2-amino-4-(4-fluorobenzylamino)-phenyl]carbamic acid ethyl ester) in modulating the KCNQ2/3 potassium channels in oocytes in a 3-fold manner, i.e. retigabine shifts the voltage dependence of channel activation to more hyperpolarized membrane potentials, increases the rate of channel activation and slows channel deactivation.

U.S. Pat. Nos. 5,849,789 and 5,852,053 (both to Rostock et al.) teaches the use of retigabine for the treatment of neurodegenerative disorders, including those associated with stroke.

U.S. Pat. No. 5,914,425 (Meisel et al.) teaches novel crystalline forms of retigabine.

U.S. Pat. No. 6,117,900 teaches the use of retigabine, also known as N-[2-amino4-(4-fluorobenzylamino)-phenyl] carbamic acid ethyl ester, for the treatment of neuropathic pain.

DESCRIPTION OF THE INVENTION

This invention comprises methods for modulating urinary bladder tissues in a mammal, particularly including uses thereof for maintaining urinary bladder control, the methods comprising administering to a mammal in need thereof a pharmaceutically effective amount of a compound which acts as an agonist or opener of the KCNQ family of potassium channels, including the KCNQ2, KCNQ3, KCNQ4, and KCNQ5 potassium channels, alone or in combination. A particular embodiment of this invention includes use in the methods described herein of one or more agonists or openers of KCNQ2/3 potassium channels. Another series of methods of this invention comprises use of one or more agonists or openers of KCNQ3/5 potassium channels.

Among the compounds useful in the methods of this invention are those disclosed in U.S. Pat. No. 5,384,330 (Dieter et al.), the contents of which are incorporated herein by reference. The compounds include those of the formula:

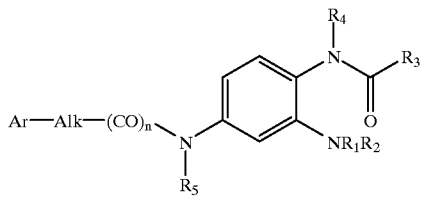

wherein:
$R_1$ is selected from hydrogen, $C_1$–$C_6$-alkyl, $C_2$–$C_6$-alkanoyl or the radical Ar;

$R_2$ is selected from hydrogen or $C_1$–$C_6$-alkyl;

$R_3$ is selected from $C_1$–$C_6$-alkoxy, $NH_2$, $C_1$–$C_6$-alkylamino, $C_1$–$C_6$-dialkylamino, amino substituted by the radical Ar, $C_1$–$C_6$-alkyl, $C_2$–$C_6$-alkenyl, $C_2$–$C_6$-alkynyl, the radical Ar or the radical ArO—;

$R_4$ is selected from hydrogen, $C_1$–$C_6$-alkyl or the radical Ar;

$R_5$ is selected from hydrogen or $C_1$–$C_6$-alkyl or the radical Ar;

Alk indicates a straight or branched alkylene group with 1–9 carbon atoms, which can also be substituted by the radical Ar;

Ar is a phenyl radical substituted by the radicals $R_6$, $R_7$ and/or $R_8$ where these radicals $R_6$, $R_7$ and $R_8$ are the same or different and represent H, $C_1$–$C_6$-alkyl, $C_3$–$C_7$cycloalkyl, hydroxy, $C_1$–$C_6$-alkoxy, $C_2$–$C_6$-alkanoyloxy, halogen, hydroxy, $C_1$–$C_6$-halogenoalkyl, —CN, —$NH_2$, —NH—$C_1$–$C_6$-alkyl, —N($C_1$–$C_6$-alkyl)$_2$, —$CO_2H$, —CO—$C_1$–$C_6$-alkyl, —CO—O—

C₁–C₆-alkyl, —COAr, —CO—OAr, —CONH₂, —CONH—C₁–C₆-alkyl, —CON(C₁–C₆-alkyl)₂, —CONHAr, —NH—CO—C₁–C₆-alkyl, —NHCO—Ar, —NHCO—C₁–C₆-alkoxy, —N—H—CO—Ar, —NHCO—NH₂, —NHCO—N(—C₁–C₆-alkyl)₂, —NHCO—NHAr, —NH—SO₂-C₁–C₆-alkyl, —NH—SO₂Ar, —NH—SO₂-nitrophenyl, —SO₂—OH, —SO₂-C₁–C₆-alkyl, —SO₂—Ar, —SO₂-C₁–C₆-alkoxy, —SO₂—OAr, —SO₂—NH₂, —SO₂—NH—C₁–C₆-alkyl, —SO₂—N(C₁–C₆-alkyl)₂, —SO₂—NHAr, —SO₂-C₁–C₆-alkoxy;

n: or 1;

The alkyl groups, halogenalkyl groups, alkenyl groups, alkynyl groups, alkoxy groups, alkylamino groups, alkanoyl amino groups, alkanoyloxy groups and alkanoyl groups in general can be straight or branched. The same also applies to alkyl and alkyloxy groups (=alkoxy groups) if these are components of more complicated radicals for example in the form of a monoalkyl- or dialkylamino group, alkanoylamino group, carbalkoxy group, alkylcarbonyl group and analogous groups. The $C_3$–$C_7$-cycloalkyl group is preferably cyclopentyl or cyclohexyl. $C_2$–$C_6$-alkenyl preferably represents allyl. $C_2$–$C_6$-alkynyl preferably represents propargyl.

The halogen atoms are chlorine, bromine or fluorine, in particular chlorine of fluorine. The alkyl and alkoxy groups as such or as components of groups of more complicated radicals consist in particular of 1–4 carbon atoms, preferably 1 or 2 carbon atoms. Alkanoyl groups, such as alkanoylamino groups or alkanoyloxy groups consist in particular of 2–4, preferably 2–3 carbon atoms. Alk consists in particular of 1–3, preferably 1 or 2 carbon atoms.

Among the more preferred compounds of this group are:

2-Amino-4-(4-fluorobenzylamino)-1-ethoxycarbonylaminobenzene;

2-Amino-4-(4-trifluoromethylbenzylamino)-1-ethoxycarbonylamino-benzene;

2-Amino-4-benzylamino-1-ethoxycarbonylamino-benzene;

2-Amino-4-(3,5-dichlorobenzylamino)-1-ethoxycarbonylamino benzene;

2-Amino-4-(3,5-dichlorobenzylamino)-1-propyloxycarbonylamino benzene;

2-Amino-(2-chlorobenzylamino)-1-(diethylcarbamoylamino) benzene;

2-Amino-4-(2,4-dichlorobenzylamino)-1-(dimethylcarbamoylamino) benzene; and 1,2-Diacetylamino-4-(4-fluorobenzylamino) benzene;

Among the most preferred compounds for use in the methods of this invention are N-[2-amino-4-(4-fluorobenzylamino)-phenyl]carbamic acid and its pharmaceutically acceptable salts and ester forms. Of particular preference is retigabine, also known as N-[2-amino-4-(4-fluorobenzylamino)-phenyl]carbamic acid ethyl ester (CAS Registry No. 150812-12-7), having the formula:

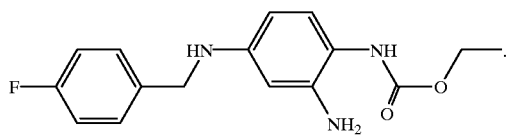

Also useful in the methods of this invention are the metabolite forms of retigabine which may be isolated from blood, urine or feces of recipients of N-[2-amino-4-(4-fluorobenzylamino)-phenyl]carbamic acid ethyl ester. The metabolites include the glucoside of retigabine, [4-(4-Fluoro-benzylamino)-2-(3,4,5-trihydroxy-6-hydroxymethyl-tetrahydropyran-2-ylamino)-phenyl]-carbamic acid ethyl ester, as well as its two glucoronide analogs, 6-[2-Ethoxycarbonylamino-5-(4-fluoro-benzylamino)-phenylamino]-3,4,5-trihydroxy-tetrahydro-pyran-2-carboxylic acid and 6-[(3-Amino-4-ethoxycarbonylamino-phenyl)-(4-fluoro-benzyl)-amino]-3,4,5-trihydroxy-tetrahydro-pyran-2-carboxylic acid. Further metabolites include N-[2-Amino4-(4-fluoro-benzylamino)-phenyl]acetamide, its cyclized analog (4-Fluoro-benzyl)-2-methyl-1H-benzoimidazol-5-yl)amine and the glucoronide analogs of N-[2-Amino-4-(4-fluoro-benzylamino)-phenyl] acetamide, 6-[(4-Acetylamino-3-amino-phenyl)-(4-fluoro-benzyl)-amino]-3,4,5-trihydroxy-tetrahydro-pyran-2-carboxylic acid and 6-[2-Acetylamino-5-(4-fluoro-benzylamino)-phenylamino]-3,4,5-trihydroxy-tetrahydro-pyran-2-carboxylic acid.

Also useful in the methods of this invention are the compounds disclosed in U.S. Pat. No. 5,565,483 (Hewawasam et al.), which issued on Oct. 15, 1996, the contents of which are incorporated herein by reference. These compounds include the substituted 3-phenyl oxindole compounds having the formulae:

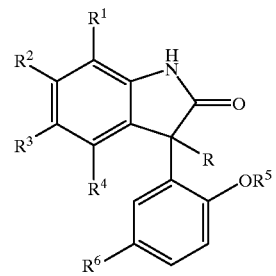

wherein:

R is hydrogen, hydroxy or fluoro;

$R^1$, $R^2$, $R^3$ and $R^4$ each are independently hydrogen, $C_{1-4}$ alkyl, halogen, trifluoromethyl, phenyl, p-methylphenyl or p-trifluoromethylphenyl; or $R^1$ and $R^2$, $R^2$ and $R^3$ or $R^3$ and $R^4$ are joined together to form a benzo fused ring;

$R^5$ is hydrogen or $C_{1-4}$ alkyl; and $R^6$ is chlorine or trifluoromethyl;

or a nontoxic pharmaceutically acceptable salt, solvate or hydrate thereof.

One group of the substituted 3-phenyl oxindole compounds useful with this invention include those described above wherein R is hydrogen. Another subgroup of these compounds include those in which $R^1$, $R^2$, $R^3$ and $R^4$ are each independently selected from H, $C_1$ to $C_4$ alkyl, halogen or trifluoromethyl, and when $R^1$ and $R^4$ are H; $R^2$ or $R^3$ is phenyl, p-methoxyphenyl or trifluormethylphenyl; or $R^1$ and $R^2$, $R^2$ and $R^3$, or $R^3$ and $R^4$ are joined together to form a benzo fused ring; $R^5$ is H or $C_1$ to $C_4$ alkyl; and $R^6$ is chlorine or trifluoromethyl, or a pharmaceutically acceptable salt form thereof.

Non-limiting examples of these substituted 3-phenyl oxindole compounds are:

(±)-3-(5–Chloro-2-methoxyphenyl)-1,3-dihydro-3-hydroxy-6-(trifluoromethyl)-2H-indol-2-one;

(±)-3-(5–Chloro-2-methoxyphenyl)-1,3-dihydro-6-(trifluoromethyl)-2H-indol-2-one;

(±)-3-(5–Chloro-2-hydroxyphenyl)-1,3-dihydro-3-hydroxy-6-(trifluoromethyl)-2H-indol-2-one;

(±)-3-(5-Chloro-2-hydroxyphenyl)-1,3-dihydro-6-(trifluoromethyl)-2H-indol-2-one;
(±)-3-(5-Chloro-2-hydroxyphenyl)-4,6-dichloro-1,3-dihydro-3-hydroxy-2-H-indol-2-one;
(±)-3-(5-Chloro-2-hydroxyphenyl)-1,3-dihydro-3-hydroxy-7-(trifluoromethyl)-2H-indol-2-one;
(±)-3-(5-Chloro-2-hydroxyphenyl)-1,3-dihydro-3-hydroxy4-trifluoromethyl)2H-indol-2-one;
(±)-1,3-Dihydro-3-hydroxy-3-[2-hydroxy-5-(trifluoromethyl)phenyl]-6-(trifluoromethyl)-2H-indol-2-one;
(±)-3-(5-Chloro-2-hydroxyphenyl)-1,3-dihydro-3-hydroxy-4,6-bis(trifluoromethyl)-2H-indol-2-one;
(−)-3-(5-Chloro-2-methoxyphenyl)-1,3-dihydro-3-hydroxy-6-(trifluoromethyl)-2H-indol-2-one;
(±)-3-(5-Chloro-2-hydroxyphenyl)-1,3-dihydro-3-hydroxy-6-(trifluoromethyl)2H-indol-2-one;
(−)-3-(5-Chloro-2-hydroxyphenyl)-1,3-dihydro-3-hydroxy-6-(trifluoromethyl)2H-indol-2-one;
(±)-3-(5-Chloro-2-methoxyphenyl)-1,3-dihydro-3-fluoro-6-(trifluoromethyl)2H-indol-2-one;
(±)-3-(5-Chloro-2-hydroxyphenyl)-1,3-dihydro-3-hydroxy-2H-benz[g]indol-2one;
(±)-3-(5-Chloro-2-hydroxyphenyl)-1,3-dihydro-6-phenyl-2H-indol-2-one;
(±)-3-(5-Chloro-2-.hydroxyphenyl)-1,3-dihydro-2H-benz[g]indol-2-one;
(±)-3-(5-Chloro-2-methoxyphenyl)-1,3-dihydro-3-fluoro-6-phenyl-2H-indol-2-one;
(±)-3-(5-Chloro-2-methoxyphenyl)-1,3-dihydro-3-fluoro-6-iodo-2H-indol-2one;
(±)-3-(5-Chloro-2-hydroxyphenyl)-1,3-dihydro-6-(4-methylphenyl)-2H-indol-2-one;
(±)-3-(5-Chloro-2-methoxyphenyl)-1,3-dihydro-3-fluoro-7-(trifluoromethyl)-2H-indol-2-one;
(±)-3-(5-Chloro-2-hydroxyphenyl)-1,3-dihydro-2H-benz[e]indol-2-one;
(±)-3-(5-Chloro-2-methoxyphenyl)-1,3-dihydro-3-fluoro-5-methyl-2H-indol-2-one;
(±)-3-(5-Chloro-2-methoxyphenyl)-1,3-dihydro-3-fluoro4,6-bis(trifluoromethyl)-2H-indol-2-one;
(±)-5-Bromo-3-(5-chloro-2-methoxyphenyl)-1,3-dihydro-3-fluoro-2H-indol-2one;
(±)-3-(5-Chloro-2-hydroxyphenyl)-1,3-dihydro-6-[4-(trifluoromethyl)phenyl]-2H-indol-2-one;
(±)-3-(5-Chloro-2-hydroxyphenyl)-1,3-dihydro-2H-indol-2-one;
(±)-5-Bromo-3-(5-chloro-2-methoxyphenyl)-1,3-dihydro-3-hydroxy-2H-indol-2-one;
(±)-3-(5-Chloro-2-hydroxyphenyl)4,6-dichloro-1,3-dihydro-2H-indol-2-one;
(±)-3-(5-Chloro-2-methoxyphenyl)-1,3-dihydro-3-hydroxy-6-iodo-2H-indol-2-one;
(±)-3-(5-Chloro-hydroxyphenyl)-1,3-dihydro-6-iodo-2H-indol-2-one;
(±)-3-(5-Chloro-2-methoxyphenyl)-1,3-dihydro-3-hydroxy-2H-benz[f]indol-2one;
(±)-3-(5-Chloro-2-hydroxyphenyl)-1,3-dihydro-3-hydroxy-2H-benz[f]indol-2one; and
(±)-3-(5-Chloro-2-hydroxyphenyl)-1,3-dihydro-2H-benz[f]indol-2-one;
and the pharmaceutically acceptable salt forms thereof.

Among the more preferred compounds of this group are:

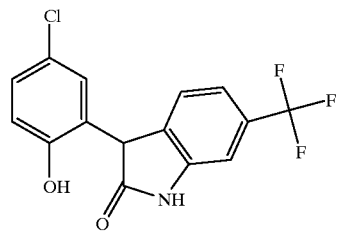

(±)-3-(5-Chloro-2-hydroxyphenyl)-1,3-dihydro-6-(trifluoromethyl)-2H-indol-2-one;

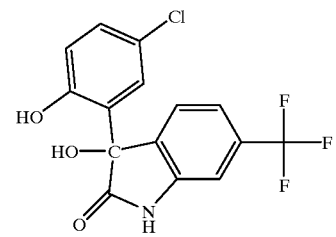

(±)-3-(5-Chloro-2-hydroxyphenyl)-1,3-dihydro-3-hydroxy-6-(trifluoromethyl)-2H-indol-2-one;

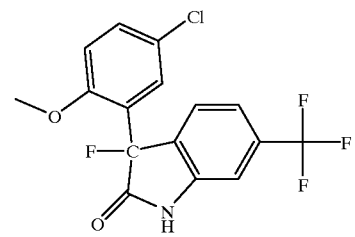

(±)-3-(5-Chloro-2-methoxyphenyl)-1,3-dihydro-3-fluoro-6-(trifluoromethyl)-2H-indol-2-one;

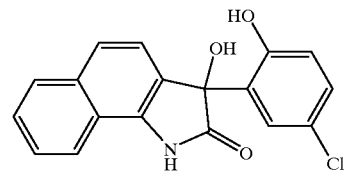

(±)-3-(5-Chloro-2-hydroxyphenyl)-1,3-dihydro-3-hydroxy-2H-benz[g]indol-2-one;

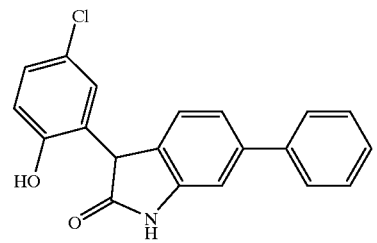

(±)-3-(5-Chloro-2-hydroxyphenyl)-1,3-dihydro-6-phenyl-2H-indol-2-one; and

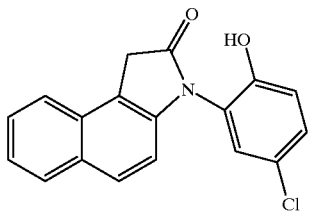

(±)-3-(5–Chloro-2-hydroxyphenyl)-1,3-dihydro-2H-benz[e]indol-2-one.

Pharmaceutically acceptable salt forms of these substituted 3-phenyl oxindole compounds include those formed as base addition, including those formed using suitable inorganic bases, such as alkali and alkaline earth metal bases, such as sodium, potassium, magnesium and calcium metallic cations. The compounds may be administered as described in U.S. Pat. No. 5,565,483. A pharmaceutically effective amount in mammals, including man, may be from about 0.1 pg/kg to about 100 mg/kg of body weight. Parenteral administration may be completed at an effective dose of from about 1 pg/kg to about 10 mg/kg of body weight.

The methods of this invention are useful for inducing, assisting or maintaining desirable bladder control in a mammal experiencing or susceptible to bladder instability or urinary incontinence. These methods include prevention, treatment or inhibition of bladder-related urinary conditions and bladder instability, including idiopathic bladder instability, nocturnal enuresis, nocturia, voiding dysfunction and urinary incontinence. Also treatable or preventable with the methods of this invention is bladder instability secondary to prostate hypertrophy. The compounds described herein are also useful in promoting the temporary delay of urination whenever desirable. The compounds of this invention may also be utilized to stabilize the bladder and treat or prevent incontinence which urge urinary incontinence, stress urinary incontinence or a combination of urge and stress incontinence in a mammal, which may also be referred to as mixed urge and stress incontinence. These methods include assistance in preventing or treating urinary incontinence associated with secondary conditions such as prostate hypertrophy.

These methods may be utilized to allow a recipient to control the urgency and frequency of urination. The methods of this invention include the treatment, prevention, inhibition and amelioration of urge urinary incontinence also known as bladder instability, neurogenic bladder, voiding dysfunction, hyperactive bladder, detrusor overactivity, detrusor hyper-reflexia or uninhibited bladder.

As described above, methods of this invention include treatments, prevention, inhibition or amelioration of hyperactive or unstable bladder, neurogenic bladder, sensory bladder urgency, or hyperreflexic bladder. These uses include, but are not limited to, those for bladder activities and instabilities in which the urinary urgency is associated with prostatitis, prostatic hypertrophy, interstitial cystitis, urinary tract infections or vaginitis. The methods of this invention may also be used to assist in inhibition or correction of the conditions of Frequency-Urgency Syndrome, and lazy bladder, also known as infrequent voiding syndrome.

The methods of this invention may also be used to treat, prevent, inhibit, or limit the urinary incontinence, urinary instability or urinary urgency associated with or resulting from administrations of other medications, including diuretics, vasopressin antagonists, anticholinergic agents, sedatives or hypnotic agents, narcotics, alpha-adrenergic agonists, alpha-adrenergic antagonists, or calcium channel blockers.

The methods of this invention are useful for inducing or assisting in urinary bladder control or preventing or treating the maladies described herein in humans in need of such relief, including adult and pediatric uses. However, they may also be utilized for veterinary applications, particularly including canine and feline bladder control methods. If desired, the methods herein may also be used with farm animals, such as ovine, bovine, porcine and equine breeds.

The applications may utilize conventional oral, rectal, parenteral or intravenous delivery methods as conventionally utilized in veterinary practice. Most preferable in most instance for home use with companion animals are oral tablets or capsules or neat compound or powdered or granular pharmaceutical formulations which may be mixed with chewable or liquid veterinary formulations or food materials or liquids acceptable to the animal in question.

As used herein, the terms "pharmaceutically effective amount" or "therapeutically effective amount" mean the total amount of each active component of the pharmaceutical composition or method that is sufficient to show a meaningful patient benefit, i.e., treatment, prevention or amelioration of urinary incontinence or the excessive or undesirable urge to urinate, or a decrease in the frequency of incidence of urinary incontinence. When applied to an individual active ingredient, administered alone, the term refers to that ingredient alone. When applied to a combination, the term refers to combined amounts of the active ingredients that result in the therapeutic effect, whether administered in combination, serially or simultaneously.

The methods of this invention may be accomplished with a daily dose of the active compounds described above from U.S. Pat. No. 5,384,330 of from about 0.1 mg/kg to about 10 mg/kg. Doses may be administered as a single regimen, such as only prior to bedtime or before travel, or as a continuous regimen divided by two or more doses over the course of a day. Human administration may be at dosages of from about 10 mg BID to about 1000 mg BID, preferably from about 50 mg BID to about 500 mg BID, more preferably at a dose of from about 100 mg BID to about 300 mg BID.

The KCNQ potassium channel agonists of this invention may also be administered in the methods of this invention in combination with pharmaceutically effective amounts of other medicinal agents useful for bladder control or the treatment or inhibition of urinary incontinence. For instance, the compounds may be administered with desmopressin acetate, available as DDAVP® Nasal Spray and DDAVP® tablets from Aventis Pharmaceuticals, as well as a desmopressin acetate rhinal tube from Ferring Pharmaceuticals Inc. Other combination products include tolterodine tartrate (available as DETROL™ tablets from Pharmacia & Upjohn), oxybutinin chloride (available in the form of DITROPAN® tablets and syrup and DITROPAN XL® extended release tablets from ALZA Pharmaceuticals), propantheline bromide (available in tablet form from Roxane Laboratories, Inc.), hyoscyamine and hyoscyamine sulfate (available, respectively, as CYSTOPAZ® tablets and CYSTOPAZ-M® timed release capsules from PolyMedica Pharmaceuticals (U.S.A.), Inc.), hyoscyamine hydrobromide, flavoxate HCl (available in URISPAS® 100 mg tablets from ALZA Pharmaceuticals), imipramine HCl (available in 10 mg, 25 mg and 50 mg tablets from Geneva Pharmaceuticals, Inc.), phenylpropanolamine, midodrine HCl (available in 2.5 mg and 5 mg PROAMATINE® tablets from Shire US Inc.), phenoxybenzamine HCl (available as DIBENZYLINE® capsules from WellSpring Pharmaceuticals Corporation), and prazosin HCl (available in MINI- PRESS® capsules from Pfizer Inc.). Each of these medicaments may be administered in the pharmaceutically effective amounts and regimens known in the art, including those listed in the Physicians' Desk Reference, 55 Edition, 2001, published by Medical Economics Company, Inc. at Monvale, N.J. 07645-1742, the relevant portions of which are incorporated herein by reference. The KCNQ channel agonists of this invention may also be used in conjunction with one or more compounds which act as vasopressin agonists including, but not limited to those described in U.S. Pat. No. 6,194,407 (Failli et al.), U.S. Pat. No. 6,090,803 (Failli et al.), U.S. Pat. No. 6,096,736 (Ogawa et al.), and U.S. Pat. No. 6,096,735 (Ogawa et al.).

Compounds as described in U.S. Pat. No. 5,384,330, including retigabine, can be administered orally using conventional pharmaceutical excipients or carriers, preferably coated or contained in hard or soft gelatin capsules. Examples of oral formulations contained in hard gelatin capsules can include those in which the active compound comprises from about 45% to 50%, by weight, of the formulation. Microcrystalline cellulose comprises from about 43% to about 47%, povidone comprises from about 3% to about 4%, and silicon dioxide and magnesium stearate each comprise from about 0.3% to about 0.7%, each by weight. Specific examples of capsules containing 50 mg, 100 mg and 200 mg may be formulated utilizing the following lists of components.

| Ingredient | Amount/Capsule |
|---|---|
| 50 mg Retigabine Capsules | |
| Retigabine | 50.0 mg |
| Microcrystalline Cellulose, NF | 45.5 mg |
| Povidone, USP | 3.5 mg |
| Silicon Dioxide, Colloidal, anhydrous, NF | 0.5 mg |
| Magnesium Stearate, EP | 0.5 mg |
| Theoretical Fill Weight | 100 mg |
| 100 mg Retigabine Capsules | |
| Retigabine | 100 mg |
| Microcrystalline Cellulose, NF | 91.0 mg |
| Povidone, USP | 7.0 mg |
| Silicon Dioxide, Colloidal, anhydrous, NF | 1.0 mg |
| Magnesium Stearate, EP | 1.0 mg |
| Theoretical Fill Weight | 200 mg |
| 200 mg Retigabine Capsules | |
| Retigabine | 200.0 mg |
| Microcrystalline Cellulose, NF | 182.0 mg |
| Povidone, USP | 14.0 mg |
| Silicon Dioxide, Colloidal, anhydrous, NF | 2.0 mg |
| Magnesium Stearate, EP | 2.0 mg |
| Theoretical Fill Weight | 400 mg |

The ingredients in the formulations above can be prepared using the following steps.

1) Weigh separately the active ingredient (retigabine), preferably screened through an 800 micron screen, and the microcrystalline cellulose components.

2) Prepare a granulation solution by dissolving the Povidone, USP in purified water.

3) Place the ingredients from Step 1 into a suitable blender and mix thoroughly.

4) Screen the mixture from Step 3 through a 1000 $\mu$m screen and place the screened mixture into the vessel of a fluidized bed granulator.

5) Heat the ingredients in the fluid bed granulator up to 27° C. product temperature while mixing.

6) Add the granulation solution from Step 2 to the fluid bed.

7) Dry the granulate in the fluid bed.

8) Weigh the colloidal silicon dioxide component, preferably screened through a 1000 $\mu$m screen, and the magnesium stearate component, preferably screened through a 600 $\mu$m screen.

9) Add the silicon dioxide and magnesium stearate components to the fluid bed granulator's vessel containing the dried granulate from Step 7 and mix the components thoroughly.

10) Screen the mixed components from Step 9, preferably through a 800 $\mu$m screen.

11) Transfer the final screened components into a suitable blender and mix thoroughly.

The final component mixture from Step 11 can then be coated, encapsulated or compressed into tablets utilizing conventional tablet excipients or carriers, as desired. It will be understood that oral dosage forms within the scope of this invention can be prepared using the components listed above in respective amounts according the dose of active ingredient in the particular formulation. For veterinary uses, the final mixture of Step 11 can be administered neat or mixed into foods acceptable to the animal in question. Further, the mixtures can be formulated into tablets, capsules or coated products, as described above, or integrated into conventional veterinary medicaments or food products.

For intravenous administration, the compounds from U.S. Pat. No. 5,384,330 described herein may be prepared and maintained in conventional lyophylized formulations and reconstituted prior to administration with an intravenously acceptable saline solution, such as a 0.9% saline solution. The pH of the intravenous formulation can be adjusted, as needed, with an intravenous and pharmaceutically acceptable acid, such as methanesulfonic acid.

KNCQ1, 3 and 5 Expression and M-current Activity in Rat Urinary Bladder

Using quantitative rtPCR, the expression of KCNQ1, KCNQ3 and KCNQ5 potassium channels was identified in the rat urinary bladder. The highest levels of expression were seen in KCNQ5 (0.2±0.1 ng KCNQ5 mRNA/GAPDH mRNA). To further probe M-current activity in the bladder, retigabine (10 $\mu$M, M-current agonist) was tested in isolated bladder smooth muscle cells using standard patch-clamp techniques. Exposure to retigabine significantly increased an outward current that was insensitive to iberiotoxin and was associated with a membrane hyperpolarization of 17.8±3.0 mV (n=5). This hyperpolarization was reversed by the addition of linopirdine (50 $\mu$M an M-current antagonist) to the tissue bath. Retigabine relaxed isolated carbachol contracted rat bladder strips with an $IC_{50}$ of 3.5±0.9 $\mu$M (n=14). This relaxation was reversed by the M-current blockers linopirdine and XE-991.

What is claimed:

1. A method of inducing or maintaining bladder control in a mammal, the method comprising administering to a mammal in need thereof a pharmacologically effective amount of a KCNQ potassium channel agonist.

2. The method of claim 1 wherein the KCNQ potassium channel is a KCNQ4 potassium channel.

3. The method of claim 1 wherein the KCNQ potassium channel is a KCNQ2/3 potassium channel.

4. The method of claim 1 wherein the KCNQ potassium channel is a KCNQ3/5 potassium channel.

5. A method of treatment or prevention of urinary incontinence in a mammal, the method comprising administering to a mammal in need thereof a pharmacologically effective amount of a KCNQ potassium channel agonist.

6. The method of claim 4 wherein the KCNQ potassium channel is a KCNQ2/3 potassium channel.

7. The method of claim 4 wherein the KCNQ potassium channel is a KCNQ3/5 potassium channel.

8. The method of claim 4 wherein the mammal is a human.

9. The method of claim 5 wherein the mammal is feline or canine.

10. A method of treatment or prevention of urinary incontinence in a mammal, the method comprising administering to a mammal in need thereof a pharmacologically effective amount of a compound of the formula:

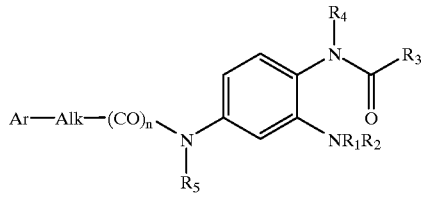

wherein:
- $R_1$ is selected from hydrogen, $C_1$–$C_6$-alkyl, $C_2$–$C_6$-alkanoyl or the radical Ar;
- $R_2$ is selected from hydrogen or $C_1$–$C_6$-alkyl;
- $R^3$ is selected from $C_1$–$C_6$-alkoxy, $NH_2$, $C_1$–$C_6$-alkylamino, $C_1$–$C_6$-dialkylamino, amino substituted by the radical Ar, $C_1$–$C_6$-alkyl, $C_2$–$C_6$-alkenyl, $C_2$–$C_6$-alkynyl, the radical Ar or the radical ArO—;
- $R_4$ is selected from hydrogen, $C_1$–$C_6$-alkyl or the radical Ar;
- $R_5$ is selected from hydrogen or $C_1$–$C_6$-alkyl or the radical Ar; Alk: a straight or branched alkylene group with 1–0 carbon atoms, which can also be substituted by the radical Ar;
- Ar is a phenyl radical substituted by the radicals $R^6$, $R_7$ and/or $R_8$ where these radicals $R_6$, $R_7$ and $R_8$ are the same or different and represent $C_1$–$C_6$-alkyl, $C_3$–$C_7$-cycloalkyl, hydroxy, $C_1$–$C_6$-alkoxy, $C_2$–$C_6$-alkanoyloxy, halogen, hydroxy, $C_1$–$C_6$-halogenoalkyl, —CN, —$NH_2$, —NH—$C_1$–$C_6$-alkyl, —N($C_1$–$C_6$-alkyl)$_2$, —$CO_2H$, —CO—$C_1$–$C_6$-alkyl, —CO—O—$C_1$–$C_6$-alkyl, —COAr, —CO—OAr, —$CONH_2$, —CONH—$C_1$–$C_6$-alkyl, —CON($C_1$–$C_6$-alkyl)$_2$, —CONHAr, —NH—CO—$C_1$–$C_6$-alkyl, —NHCO—Ar, —NHCO—$C_1$–$C_6$-alkoxy, —N—H—CO—Ar, —NHCO—$NH_2$, —NHCO—N(—$C_1$–$C_6$-alkyl)$_2$, —NHCO—NHAr, —NH—$SO_2$—C—1—$C_6$-alkyl, —NH—$SO_2$Ar, —NH—$SO_2$-nitrophenyl, —$SO_2$—OH, —$SO_2$-$C_1$–$C_6$-alkyl, —$SO_2$—Ar, —$SO_2$-$C_1$–$C_6$-alkoxy, —$SO_2$—OAr, —$SO_2$—$NH_2$, —$SO_2$—NH—$C_1$–$C_6$-alkyl, —$SO_2$—N($C_1$–$C_6$-alkyl)$_2$, —$SO_2$—NHAr, —$SO_2$—$C_2$–$C_6$-alkoxy;
- n is 0 or 1;

or a pharmaceutically acceptable salt thereof.

11. The method of claim 10, wherein the compound is selected from the group consisting of:
- 2-Amino-4-(4-fluorobenzylamino)-1-ethoxycarbonylaminobenzene;
- 2-Amino-4-(4-trifluoromethylbenzylamino)-1-ethoxycarbonylamino-benzene;
- 2-Amino-4-benzylamino-1-ethoxycarbonylamino-benzene;
- 2-Amino-4-(3,5-dichlorobenzylamino)-1-ethoxycarbonylamino benzene;
- 2-Amino-4-(3,5-dichlorobenzylamino)-1-propyloxycarbonylamino benzene;
- 2-Amino-(2-chlorobenzylamino)-1-(diethylcarbamoylamino) benzene;
- 2-Amino-4-(2,4-dichlorobenzylamino)-1-(dimethylcarbamoylamino) benzene; or
- 1,2-Diacetylamino-4-(4-fluorobenzylamino) benzene;

or a pharmaceutically acceptable salt thereof.

12. The method of claim 10 wherein the mammal is a human.

13. The method of claim 5 wherein the mammal is feline or canine.

14. The method of claim 10 wherein the urinary incontinence is urge incontinence.

15. A method of treatment or inhibition of urinary incontinence in a mammal, the method comprising administering to a mammal in need thereof a pharmacologically effective amount of N-[2-amino4-(4-fluorobenzylamino)-phenyl] carbamic acid or a pharmaceutically acceptable salt or ester form thereof.

16. The method of claim 15 wherein the pharmaceutically acceptable ester form is N-[2-amino-4-(4-fluorobenzylamino)-phenyl]carbamic acid ethyl ester.

17. The method of claim 15 wherein the mammal is a human.

18. The method of claim 15 wherein the mammal is feline or canine.

19. The method of claim 15 wherein the urinary incontinence is urge incontinence.

20. The method of claim 15 wherein the urinary incontinence is secondary to prostate hypertrophy.

21. The method of claim 15 wherein the urinary incontinence is mixed urge and stress incontinence.

22. The method of claim 15 wherein the a pharmacologically effective amount is from about 0.1 mg/kg to about 10 mg/kg.

23. The method of claim 15 wherein the a pharmacologically effective amount is from about 10 mg BID to about 1000 mg BID.

24. The method of claim 15 wherein the a pharmacologically effective amount is from about 50 mg BID to about 500 mg BID.

25. The method of claim 15 wherein the a pharmacologically effective amount is from about 100 mg BID to about 300 mg BID.

26. A method of treatment or inhibition of urinary incontinence in a mammal, the method comprising administering to a mammal in need thereof a pharmacologically effective amount of a compound of the formula:

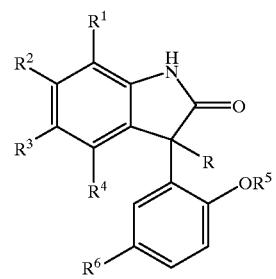

wherein:
- R is hydrogen, hydroxy or fluoro;
- $R^1$, $R^2$, $R^3$ and $R^4$ each are independently hydrogen, $C_{1-4}$ alkyl, halogen, trifluoromethyl, phenyl, p-methylphenyl or p-trifluoromethylphenyl; or $R^1$ and $R^2$, $R^2$ and $R^3$ or $R^3$ and $R^4$ are joined together to form a benzo fused ring;

$R^5$ is hydrogen or $C_{1-4}$ alkyl; and $R^6$ is chlorine or trifluoromethyl; or a nontoxic pharmaceutically acceptable salt, solvate or hydrate thereof.

27. The method of treatment or inhibition of urinary incontinence in a mammal of claim 26 wherein the compound is selected from the group consisting of:

(±)-3-(5Chloro-2-methoxyphenyl)-1,3-dihydro-3-hydroxy-6-(trifluoromethyl)-2H-indol-2-one;

(±)-3-(5-Chloro-2-methoxyphenyl)-1,3-dihydro-6-(trifluoromethyl)-2H-indol-2-one;

(±)-3-(5-Chloro-2-hydroxyphenyl)-1,3-dihydro-3-hydroxy-6-(trifluoromethyl)-2H-indol-2-one;

(±)-3-(5-Chloro-2-hydroxyphenyl)-1,3-dihydro-6-(trifluoromethyl)-2H-indol-2-one;

(±)-3-(5-Chloro-2-hydroxyphenyl)-4,6-dichloro-1,3-dihydro-3-hydroxy-2-H-indol-2-one;

(±)-3-(5-Chloro-2-hydroxyphenyl)-1,3-dihydro-3-hydroxy-7-(trifluoromethyl)-2H-indol-2-one;

(±)-3-(5-Chloro-2-hydroxyphenyl)-1,3-dihydro-3-hydroxy-4-trifluoromethyl)2H-indol-2-one;

(±)-1,3-Dihydro-3-hydroxy-3-[2-hydroxy-5-(trifluoromethyl)phenyl]-6-(trifluoromethyl)-2H-indol-2-one;

(±)-3-(5-Chloro-2-hydroxyphenyl)-1,3-dihydro-3-hydroxy-4,6-bis(trifluoromethyl)-2H-indol-2-one;

(−)-3-(5-Chloro-2-methoxyphenyl)-1,3-dihydro-3-hydroxy-6-(trifluoromethyl)-2H-indol-2-one;

(±)-3-(5-Chloro-2-hydroxyphenyl)-1,3-dihydro-3-hydroxy-6-(trifluoromethyl)2H-indol-2-one;

(−)-3-(5-Chloro-2-hydroxyphenyl)-1,3-dihydro-3-hydroxy-6-(trifluoromethyl)2H-indol-2-one;

(±)-3-(5-Chloro-2-methoxyphenyl)-1,3-dihydro-3-fluoro-6-(trifluoromethyl)2H-indol-2-one;

(±)-3-(5-Chloro-2-hydroxyphenyl)-1,3-dihydro-3-hydroxy-2H-benz[g]indol-2one;

(±)-3-(5-Chloro-2-hydroxyphenyl)-1,3-dihydro-6-phenyl-2H-indol-2-one;

(±)-3-(5-Chloro-2-hydroxyphenyl)-1,3-dihydro-2H-benz[g]indol-2-one;

(±)-3-(5-Chloro-2-methoxyphenyl)-1,3-dihydro-3-fluoro-6-phenyl-2H-indol-2-one;

(±)-3-(5-Chloro-2-methoxyphenyl)-1,3-dihydro-3-fluoro-6-iodo-2H-indol-2one;

(±)-3-(5-Chloro-2-hydroxyphenyl)-1,3-dihydro-6-(4-methylphenyl)-2H-indol-2-one;

(±)-3-(5-Chloro-2-methoxyphenyl)-1,3-dihydro-3-fluoro-7-(trifluoromethyl)-2H-indol-2-one;

(±)-3-(5-Chloro-2-hydroxyphenyl)-1,3-dihydro-2H-benz[e]indol-2-one;

(±)-3-(5-Chloro-2-methoxyphenyl)-1,3-dihydro-3-fluoro-5-methyl-2H-indol-2-one;

(±)-3-(5-Chloro-2-methoxyphenyl)-1,3-dihydro-3-fluoro4,6-bis(trifluoromethyl)-2H-indol-2-one;

(±)-5-Bromo-3-(5-chloro-2-methoxyphenyl)-1,3-dihydro-3-fluoro-2H-indol-2one;

(±)-3-(5-Chloro-2-hydroxyphenyl)-1,3-dihydro-6-[4-(trifluoromethyl)phenyl]-2H-indol-2-one;

(±)-3-(5-Chloro-2-hydroxyphenyl)-1,3-dihydro-2H-indol-2-one;

(±)-5-Bromo-3-(5-chloro-2-methoxyphenyl)-1,3-dihydro-3-hydroxy-2H-indol-2-one;

(±)-3-(5-Chloro-2-hydroxyphenyl)-4,6-dichloro-1,3-dihydro-2H-indol-2-one;

(±)-3-(5-Chloro-2-methoxyphenyl)-1,3-dihydro-3-hydroxy-6-iodo-2H-indol-2-one;

(±)-3-(5-Chloro-hydroxyphenyl)-1,3-dihydro-6-iodo-2H-indol-2-one;

(±)-3-(5-Chloro-2-methoxyphenyl)-1,3-dihydro-3-hydroxy-2H-benz[f]indol-2one;

(±)-3-(5-Chloro-2-hydroxyphenyl)-1,3-dihydro-3-hydroxy-2H-benz[f]indol-2one; and (±)-3-(5-Chloro-2-hydroxyphenyl)-1,3-dihydro-2H-benz[f]indol-2-one;

and the pharmaceutically acceptable salt forms thereof.

28. The method of claim 26 wherein the mammal is a human.

29. The method of claim 26 wherein the mammal is feline or canine.

30. The method of claim 26 wherein the urinary incontinence is urge incontinence.

31. The method of claim 26 wherein the urinary incontinence is secondary to prostate hypertrophy.

32. The method of claim 26 wherein the urinary incontinence is mixed urge and stress incontinence.

* * * * *